United States Patent
Breitenbach et al.

(10) Patent No.: US 9,060,986 B2
(45) Date of Patent: Jun. 23, 2015

(54) DELIVERY SYSTEM FOR SUSTAINED RELEASE OF A CALCIUM-CHANNEL BLOCKING AGENT

(75) Inventors: Jorg Breitenbach, Mannheim (DE); Bernd Liepold, Dossenheim (DE); Didier R. Lefebvre, Mundelein, IL (US); Steffen Bossmann, Altleiningen (DE); Benedikt Steitz, Speyer (DE); Peter Hölig, Waechtersbach (DE)

(73) Assignee: BDS Pharma GmbH, Graz (AT)

(*) Notice: Subject to any disclaimer, the term of this patent is extended or adjusted under 35 U.S.C. 154(b) by 0 days.

(21) Appl. No.: 13/500,013

(22) PCT Filed: Oct. 5, 2010

(86) PCT No.: PCT/EP2010/064804
§ 371 (c)(1),
(2), (4) Date: Jun. 19, 2012

(87) PCT Pub. No.: WO2011/042420
PCT Pub. Date: Apr. 14, 2011

(65) Prior Publication Data
US 2012/0252851 A1    Oct. 4, 2012

(30) Foreign Application Priority Data
Oct. 6, 2009  (EP) .................................... 09172370

(51) Int. Cl.
*A61K 31/4418* (2006.01)
*A61P 25/00* (2006.01)
*A61K 31/216* (2006.01)
*A61K 9/00* (2006.01)
*A61K 9/14* (2006.01)

(52) U.S. Cl.
CPC ............. *A61K 31/216* (2013.01); *A61K 9/0024* (2013.01); *A61K 9/146* (2013.01)

(58) Field of Classification Search
None
See application file for complete search history.

(56) References Cited

U.S. PATENT DOCUMENTS

| 5,993,855 | A | * | 11/1999 | Yoshimoto et al. | .......... 424/489 |
| 2008/0305147 | A1 | | 12/2008 | Macdonald et al. | |
| 2009/0162407 | A1 | * | 6/2009 | Biggs et al. | .................. 424/401 |

FOREIGN PATENT DOCUMENTS

| EP | 0058481 A1 | 8/1982 |
| WO | 2004011054 A2 | 2/2004 |

OTHER PUBLICATIONS

Katti, Polymer Chemistry course teaching notes, pp. 1-12, http://web.missouri.edu/~kattik/katti/coursepage.html.*
Miyajima et al. (The effects of drug physic-chemical properties on release from copoly (lactic/glycolic acid) matrix, Int. J. Pharm., 1998, vol. 169, pp. 255-265).*
Mitra et al. (Effects of polymer blending on the release of ganciclovir from PLGA microspheres, Pharm. Resch., 2005, vol. 23, pp. 215-223).*
Mehta et al. in (peptide containing microsphere from low molecular weight and hydrophilic poly(d,l-lactide-co-glycolide), J. Contrl. Release, 1996, vol. 41, pp. 252, Table 1).*
Form PCT/ISA/210, Nov. 22, 2010, ISR for PCT/EP2010/064804.
Form PCT/ISA/237, Nov. 22, 2010, Written Opinion for PCT/EP2010/064804.
Kasuya H et al: "Efficacy and safety of nicardipine prolonged-release implants for preventing vasospasm in humans", 2002, Stroke 2002 US, vol. 33, NR. 4, pp. 1011-1015, XP002569450.
Soppimath K S et al: "Ethyl acetate as a dispersing solvent in the production of poly(DL-lactide-co-glycolide) microspheres: Effect of process parameters and polymer type" May 2002, Journal of Microencapsulation, vol. 19, NR 3, pp. 281-292.
Krischek et al., Neurol. Med. Chir. (Tokyo) 47: 389-396, 2007.
Kasuya et al., Neurosurgery 56: 895-902, 2005.
Pluta et al., Neurol. Res. 31: 151-158, 2009.
P.V. Sergeeva (general editor): "Kratki kurs molekulyamoi farmakologi" (Short course of molecular pharmacology), Moscow medical institute named after N.I. Pirogov, 1975(338 pages), p. 10.
L.E. Kholodov etal., Klini'cheskata farmakokinetika (Clinical pharmacokinetics), Moscow, Medizina, 1985 (464 pages), pp. 83-96, 134-136, 160, 378-380.

* cited by examiner

*Primary Examiner* — Kevin S Orwig
*Assistant Examiner* — Ping Cao
(74) *Attorney, Agent, or Firm* — Saul Ewing LLP; Peter C. Lauro, Esq.

(57) ABSTRACT

A delivery system for sustained release of a calcium-channel blocking agent is adapted for introduction in the cerebrospinal fluid of a subject. The delivery system comprises a solid dispersion product of a calcium-channel blocking agent in a mixture of a (i) first poly(lactide-co-glycolide) having a molecular weight distribution centered around a first number average molecular weight Mn1 and a (ii) second poly(lactide-co-glycolide) having a molecular weight distribution centered around a second number average molecular weight Mn2, wherein Mn1 is in the range of from 2000 to 3000 g/mol and the ratio of Mn1/Mn2 is from 1.8 to 3.5. The delivery system is deposited in the vicinity of or adjacent to a blood vessel showing vasospasm or suspected of developing vasospasm.

8 Claims, 3 Drawing Sheets

DELIVERY SYSTEM FOR SUSTAINED RELEASE OF A CALCIUM-CHANNEL BLOCKING AGENT

This application is the U.S. national phase pursuant to 35 U.S.C. §371 of international application Ser. No. PCT/EP2010/064804, filed Oct. 5, 2010, designating the United States and published in English on Apr. 14, 2011 as publication WO 2011/042420 A1, which claims priority to European application Ser. No. 09172370.0, filed Oct. 6, 2009. The entire contents of the aforementioned patent applications are incorporated herein by this reference.

FIELD OF THE INVENTION

The present invention relates to a delivery system for sustained release of a calcium-channel blocking agent, which is adapted for introduction in the cerebrospinal fluid of a subject, the delivery system for treatment or prevention of brain vasospasm, such as brain vasospasm associated with traumatic brain injury or subarachnoid hemorrhage, and to a method for the preparation of said delivery system.

PRIOR ART

Traumatic brain injury and stroke are life-threatening conditions, which require immediate drug therapy in order to prevent or ameliorate the immediate and indirect effects of these conditions. Traumatic brain injury is mainly caused by forceful, traumatic strokes to the head, which not necessarily need to be penetrating strokes. The initial trauma caused therefrom may result in expanding hematomas, subarachnoidal hemorrhage (SAH), cerebral edema, cerebral hypoxia and elevated intracranial pressure, which additionally may damage the brain by reducing cerebral blood flow. Vasospasm of brain arteries is a potential late consequence of SAH, and may occur days or even weeks after the event leading to SAH in the first place. The vasoconstriction occurring during vasospasm of brain arteries causes a reduction of the blood supply to the brain, and can lead to (temporary) ischemic strokes, thus additionally worsening the condition of the patient.

Nicardipine is a drug which frequently is delivered in such cases in order to prevent vasospasms and concomitant further reduction of blood flow in traumatic brains. The drug may be administered to patients by administering nicardipine-containing pharmaceutical compositions (as described in the US patent application 2008/0305147A) or inserting nicardipine-containing implants (e.g. described in Krischek et al., Neurol. Med. Chir. (Tokyo) 47: 389-396, 2007; Kasuya et al., Neurosurgery 56:895-902, 2005; Kasuya et al., Stroke 33: 1011-1015, 2002; and Pluta et al., Neurol. Res. 31:151-158, 2009). Currently used implants are based on copolymers of lactic and glycolic acid, which are loaded with nicardipine after dissolving both components in organic solvents, followed by evaporation of the solvent and heat compression of the copolymer/nicardipine residue (cf. Kazuya et al., 2002). However, solvents potentially remaining in the implant may pose additional health hazards to the patients and therefore necessitate thorough removal procedures. Further, during in vitro dissolution tests it was observed that the known implants did not completely dissolve. Thus, these implants may be not completely metabolized in the patients' body and leave undesired clogging residues. Moreover, the polymers used in the implants of Kazuya et al. are said to have an average molecular weight of 4000 Dalton, which corresponds to a number average molecular weight of approximately 1500 Dalton. This low number molecular weight results in a pronounced tack of the implants, which consequently are difficult to handle and, for example, may adhere to the gloves of the surgeon or the instruments used by him during the surgical procedure.

A method for preparing peptide-containing implants by dissolving copolymers of differing molecular weight together with a pharmaceutically active peptide, removing the solvent and compressing the residue has been described. However this method still relies on organic solvents (EP 0 058 481)

There is a need for implants capable of being produced by a solvent-free process and having characteristics equal or superior to known implants.

The need is met by a delivery system comprising a solid dispersion product of a calcium-channel blocking agent in a mixture of at least two copolymers of lactic acid and glycolic acid, the copolymers having two different molecular weights, and an manufacturing method for preparing said delivery system by extrusion.

SUMMARY OF THE INVENTION

In a first aspect the present invention relates to a delivery system for sustained release of a calcium-channel blocking agent, which is adapted for introduction in the cerebrospinal fluid of a subject and comprises a solid dispersion product of a calcium-channel blocking agent in a mixture of a (i) first poly(lactide-co-glycolide) having a molecular weight distribution centered around a first number average molecular weight $Mn_1$ and a (ii) second poly(lactide-co-glycolide) having a molecular weight distribution centered around a second number average molecular weight $Mn_2$, wherein $Mn_1$ is in the range of from 2000 to 3000 g/mol and the ratio of $Mn_1/Mn_2$ is from 1.8 to 3.5. Preferably, the first poly(lactide-co-glycolide) and the second poly(lactide-co-glycolide) are homogenously miscible with each other, resulting in a monophasic mixture.

According to one embodiment the weight ratio of the first poly(lactide-co-glycolide) and the second poly(lactide-co-glycolide) is from 10:1 to 1:1.5, in particular from 4:1 to 1:1.

According to one embodiment the lactate:glycolate molar ratio in the first poly(lactide-co-glycolide) is from 45:55 to 55:45.

According to one embodiment the lactate:glycolate molar ratio in the second poly(lactide-co-glycolide) is from 45:55 to 55:45. In particular, both the lactate:glycolate molar ratio in the first poly(lactide-co-glycolide) and the lactate:glycolate molar ratio in the second poly(lactide-co-glycolide) may be from 45:55 to 55:45.

According to a further embodiment the calcium-channel blocking agent constitutes 1 wt. % to 25 wt. % of the total weight of the solid dispersion product. The calcium-channel blocking agent may in particular be molecularly dispersed in the mixture.

According to particular embodiments, the calcium-channel blocking agent is nicardipine, a pharmaceutically acceptable salt, hydrate or solvate thereof. In further embodiments the delivery system will show an in vitro release profile characterized in that 4.5% to 8.5% of the total amount of nicardipine is released after 1 day, 10% to 20% of the total amount of nicardipine is released after 3 days, and 25% to 36%, of the total amount of nicardipine is released after 7 days;

when a delivery system containing the equivalent of 4 mg nicardipine is placed in a dissolution medium of phosphate buffered saline, pH 7.4, and 0.1 w/v % polysorbate 80, at 37° C. with shaking at 60 strokes per minute.

A further aspect of the invention relates to the delivery system according to the invention for the treatment or prevention of brain vasospasm, such as brain vasospasm associated with traumatic brain injury or subarachnoid hemorrhage.

A further aspect of the invention relates to a method of treatment or prevention of brain vasospasm, such as brain vasospasm associated with traumatic brain injury or subarachnoid hemorrhage, in a subject by depositing a delivery system according to the invention in the cerebrospinal fluid of the subject. In particular embodiments the delivery system is deposited in the vicinity of or adjacent to a blood vessel showing vasospasm or suspected of developing vasospasm.

A further aspect of the invention relates to a method for the preparation of a delivery system according to the invention, comprising preparing a melt of the first poly(lactide-co-glycolide), the second poly(lactide-co-glycolide) and the calcium-channel blocking agent and allowing the melt to solidify. According to one embodiment the method comprises the steps of:
a) providing a mixture of the first poly(lactide-co-glycolide), the second poly(lactide-co-glycolide) and the calcium-channel blocking agent,
b) increasing the temperature of the mixture to a first temperature T1 and maintaining the mixture at the temperature T1 in order to melt the first and the second poly(lactide-co-glycolide) and to disperse the calcium-channel blocking agent therein,
c) decreasing the temperature to a second temperature T2 and maintaining the mixture at the temperature T2 in order to adjust the viscosity of the mixture to a viscosity suitable for extrusion, and
d) forcing the mixture through a die.

The components of the mixture preferably are present as discrete particles, e.g in the form of granules or powders, or combinations thereof, in order to facilitate the homogeneous blending of the components.

DETAILED DESCRIPTION OF THE INVENTION

The invention will now be described in further detail, wherein reference is made to the accompanying figures.

Definitions

Unless defined otherwise or obvious from the context, the molecular weight of polymer is to be understood as the number average molecular weight Mn (or $M_n$).

In general, both the first poly(lactide-co-glycolide) and the second poly(lactide-co-glycolide) are monodisperse copolymers. A molecular weight distribution centered around an average value is meant to define the essentially monomodal molecular weight distribution associated with the number average value. In general, the poly(lactide-co-glycolides) have a polydispersity index (which is the quotient of the weight average molecular weight over the number average weight) of not more than 3.2. Molecular weights of polymers were measured by size exclusion chromatography (SEC). Waters HPLC equipment (Waters 515) fitted with 4 coupled Waters Styragel columns as the stationary phase, tetrahydrofuran at 1 mL/min flow rate as the mobile phase, and a Waters 410 refractometer as the detector were used. Molecular weights were expressed as number-average molecular weights (Mn) and weight-average molecular weight (Mw) with polydispersity index (PDI=Mw/Mn). Molecular weight was calculated by the system calibration software using polystyrene standards of known molecular weights.

A "monophasic mixture" of polymers means a polymer blend wherein the polymers are miscible with one another on a molecular chain level and are capable of forming a mixture that is chemically and physically uniform throughout, i.e., forming "one phase".

Brain vasospasm relates to a temporary or permanent constriction of blood vessels (in particular arteries) located anywhere in the brain. Referring to humans the brain comprises the telencephalon (in particular the cerebral cortex), the diencephalon, the mesencephalon, the metencephalon (in particular the cerebellum) and the myelencephalon. In particular, brain vasospasm relates to a temporary or permanent constriction of blood vessels of the cerebellum and the cerebrum (in particular of the cerebral cortex).

Sustained Release

In the context of the present invention sustained release of a calcium-channel blocking agent relates to an essentially uniform release of said agent over a given, prolonged period of time. Said sustained release is opposed to a burst-like release over the same prolonged period of time, wherein the majority of the active ingredient is released during one or several brief periods, which are preceded and/or followed by periods of essentially lower release (typically one early peak, during which the majority of active ingredient is released and which clearly fades until all of the active ingredient has been set free). Preferably, the prolonged periods of time, during which sustained release is maintained, encompass one day, two days, three days, four days, five days, six days, 7 days, 10 days, 12, days, 14 days, 18 days, 21 days or 28 days. In particular, sustained release is maintained for one day, 2 days, 3 days, for days, five days, six days or seven days. Encompassed within the concept of sustained release is a release profile of essentially uniform release within a first subperiod of up to 1 day, up to 2 days, up to 3 days, up to 4 days and/or up to 7 days, to be followed by a second subperiod with still essentially uniform release, although at slightly lower level. Sustained release in the context of the present invention therefore ensures an essentially uniform release of an active ingredient over time periods such as one or several days, one, two, three or four weeks.

The release curve of a delivery system may be determined in vitro by placing it in a dissolution medium, and shaking the medium. In a suitable test setup, the delivery system was added to a 500 mL Erlenmeyer flask with 250 mL of dissolution medium (phosphate buffered saline pH=7.4+0.1% w/v polysorbate 80). The Erlenmeyer flasks were placed in a GFL Shaking Incubator (model 3033) at 37° C. under gentle shaking by orbital motion (60 strokes/min). Using such an in vitro-assay, a preferred release profile of a delivery system containing 4 mg calcium-channel blocking agent, preferably nicardipine, leads to a release of 4.5% to 8.5% of the total amount of the calcium-channel blocking agent when measured after one day, 10% to 20% of the total amount of the calcium-channel blocking agent when measured after 3 days, and 25% to 36% of the total amount of the calcium-channel blocking agent when measured after 7 days. Preferably, the release of the calcium-channel blocking agent is continuous (i.e. devoid of sudden bursts or periods of lacking release) in the intervals between those time points of measuring.

Calcium-Channel Blocking Agent

The calcium-channel blocking agent is effective for treating and/or preventing brain vasospasm, such as brain vasospasm associated with traumatic brain injury or subarachnoid hemorrhage. Examples for calcium channel blockers comprise nimodipine, nifedipine, verapamil, nicardipine and isradipine. A preferred active ingredient is nicardipine. In addition to the calcium-channel blocking agent, the delivery system of the invention may additionally comprise at least one more calcium-channel blocking agent, or one or more active ingredients other than a calcium-channel blocking agent. The active ingredients may independently from each other be selected from nonsteroidal anti-inflammatory agents, steroid anti-inflammatory agents, NMDA antagonists, endothelin receptor antagonists, antioxidants, neurotrophic factors and calcium channel blockers. Examples for nonsteroidal anti-inflammatory agents comprise aspirin, acetaminophen, indomethacin and ibuprofen. Examples for steroid anti-inflammatory agents comprise cortisone, prednisone, prednisolone and dexamethasone. Examples for NMDA antagonists comprise magnesium sulfate and dextromethorphane. Examples for endothelin receptor antagonists comprise clazosentan and bosentan. Examples for antioxidants comprise superoxide dismutase, catalase, nitric oxide, mannitol, allopurinol and dimethyl sulfoxide. Examples for neurotrophic factors comprise endorphins and citicholine. In case one or more active ingredients are present in the delivery system, the preferred calcium-channel blocking agent is nicardipine.

The calcium-channel blocking agent may constitute 1 wt. % to 25 wt. % of the total weight of the solid dispersion product, such as 5 wt. % to 20 wt. %, 10 wt. % to 15 wt. %, or approximately 10 wt. %. In case more than one calcium-channel blocking agent is present, the combined total weight of all calcium-channel blocking agents may constitute 1 wt. % to 25 wt. % of the total weight of the solid dispersion product as described before.

Poly(lactide-co-glycolide)

Poly(lactide-co-glycolide) denotes a copolymer (or co-condensate) of lactic acid and glycolic acid. The poly(lactide-co-glycolide) copolymers for use in the present invention are preferably biodegradable, i.e. they degrade in an organism over time by enzymatic or hydrolytic action or by similar mechanisms, thereby producing pharmaceutically acceptable degradation products, and biocompatible, i.e. that do not cause toxic or irritating effects or immunological rejection when brought into contact with a body fluid. The lactic acid units may be L-lactic acid, D-lactic acid or a mixture of both. The proportion of lactic acid units and glycolic acids units within the copolymer may be in the range from 25:75 to 75:25 preferentially is in the range from 40:60 to 60:40, in particular 45:55 to 55:45.

The number average molecular weight $Mn1$ of the first poly(lactide-co-glycolide) is higher than the number average molecular weight $Mn2$ of second poly(lactide-co-glycolide). For example, $Mn1$ may be in the range of from 2000 to 3000 g/mol, in particular 2000 to 2500 g/mol. A preferred first poly(lactide-co-glycolide) is RESOMER® Condensate RG 50:50 Mn 2300 g/mol (commercially available from Boehringer Ingelheim, Germany) having an $Mn1$ of 2300 g/mol. The number average molecular weight $Mn2$ of the second poly(lactide-co-glycolide) may be the range from 300 to 1200 g/mol, preferably from 400 to 1000 g/mol, in particular from 600 to 1000 g/mol. A preferred second poly(lactide-co-glycolide) is RESOMER® Condensate RG 50:50 Mn 800 g/mol (commercially available from Boehringer Ingelheim, Germany), having an $Mn2$ of 800 g/mol.

Auxiliary Agents

The delivery system of the present invention can consist solely of its essential components, i.e. the calcium-channel blocking agent, the first and the second poly(lactide-co-glycolide), or may optionally comprise one or more auxiliary agents. Suitable auxiliary agents are known in the art, and examples thereof comprise antibacterial and antifungal agents, stabilizers, isotonic and pH-controlling agents. The auxiliary agents may be incorporated into the dispersion product and/or the dispersion product may be coated by auxiliary agents in order to prevent or delay chemical or physical change during storage (e.g. by penetration of moisture or oxygen) or to preserve the shape of the delivery system. The auxiliary agents preferably are biodegradable and biocompatible. Examples for suitable auxiliary agents comprise naturally derived polymers, such as albumin, alginate, cellulose derivatives, collagen, fibrin, gelatin, polysaccharides and artificial polymers such as polyesters (of polylactid acid, polylactic-polyglycolic acid), polyethylene glycol, poloxamers, polyanhydrides and polyoxamers.

Solid Dispersion Product

In the delivery system according to the invention the calcium-channel blocking agent is present as a solid dispersion or, preferably, as a solid solution. The term "solid dispersion" defines a system in a solid state (as opposed to a liquid or gaseous state) comprising at least two components, wherein one component is dispersed evenly throughout the other component or components. For example, the calcium-channel blocking agent is dispersed in a matrix comprised of the first and the second poly(lactide-co-glycolide). The term "solid dispersion" encompasses systems having small particles, typically of less than 1 µm in diameter, of one phase dispersed in another phase. When said dispersion of the components is such that the system is chemically and physically uniform or homogeneous throughout or consists of one phase (as defined in thermodynamics), such a solid dispersion will be called a "solid solution" or a "molecular dispersion". Molecular dispersions are preferred physical systems. These systems do not contain any significant amounts of active ingredients in their crystalline or microcrystalline state, as evidenced by thermal analysis (DSC) or X-ray diffraction analysis (WAXS).

Likewise, further active ingredients and auxiliary agents may be dispersed similarly as described for calcium-channel blocking agents, unless they are deposited on the surface (e.g. as coatings).

In order to provide a delivery system which is safe for use as an implant, the solid dispersion product may be sterilized by means known in the art. For example, sterilization is effected by gamma radiation.

Delivery System

The delivery system should be interpreted broadly and encompass systems commonly referred to as medical devices and drug products. Preferably, the delivery system is an implant of predetermined shape which comprises the solid dispersion product. In suitable embodiments, the delivery system consists of the solid dispersion product. The delivery systems may have a variety of shapes, such as essentially globular shapes, e.g. balls and ellipsoids, or may have an elongated shape, such as rods or tubes (with a circular cross-section), flattened tubes (with an oval cross-section), triangular, rectangular or polygonal rods or tubes (with essentially triangular, rectangular or polygonal cross-section), wherein the surfaces may have convex or concave forms. The delivery systems may in particular have shapes which mimic the surface topology of the subarachnoid compartment, and may for example have an elongated triangular shape with convex surfaces, thus facilitating their deposition and/or fixation in or on the sulci formed by cerebral gyri, or on the blood vessels in those regions. Delivery systems of desired shape may be formed by injection molding, blow molding, extrusion, or any other molding, forming or casting process known in the art to be suitable for shaping components.

Methods of Treatment

The delivery system may be applied topically to a site, where traumatic brain injury, subarachnoid hemorrhage and/or brain vasospasm is to be prevented, treated or ameliorated. In particular, the delivery systems may be implanted into those sites via methods known in the art. Examples for such methods comprise application by open surgery, deposition by microinvasive surgery, and administration by injection via canules or catheters. The delivery systems are deposited in the cerebrospinal fluid of the subject. Preferably, they are deposited in cranial cerebrospinal fluid. In particular, the delivery systems are deposited in the vicinity of a blood vessel showing vasospasm or suspected of developing vasospasm (i.e. in a macroscopically visible distance), or adjacent to such a vessel (i.e. in immediate contact or not separated by a macroscopically visible distance). Preferably, the distance between the delivery system and the vessel is minimal. Prior to their deposition, the delivery systems may be wetted or rinsed with suitable solutions. They may be administered to subjects in need thereof, in particular subject, in which traumatic brain injury, subarachnoid hemorrhage and/or brain vasospasm has occurred, is imminent or is to be prevented. Regions suspected of developing vasospasms are in particular regions directly showing traumatic brain injury or subarachnoid hemorrhage, as well as regions in the vicinity thereof, in particular those regions, which may be exposed from products or degradation products diffusing from or being transported from a region of traumatic brain injury, subarachnoid hemorrhage. The determination of useful sites for depositing delivery systems is within the skill of the physician, and may be supported by imaging methods such as computed tomography or magnetic resonance imaging. Causes for traumatic brain injury and/or subarachnoid hemorrhage may for example be external forces such as hits or penetrating objects, or internal causes, such as rupturing aneurysms, thrombotic obliteration or thrombotic occlusion, stroke, and blood vessel damage by infectious agents. Subjects in need of the medicament may be humans and animals in general, such as fish, amphibians, reptiles, birds and mammals, in particular cows, horses, sheep, goats, pigs, cats, dogs, mice and guinea pigs. The subjects may in particular be humans.

The delivery systems may be deposited once or repeatedly, e.g. in intervals of days, weeks, or months. Preferably, a deposition occurs once.

During each deposition, one or more delivery systems may be deposited in the cerebrospinal fluid of the subject. One delivery system may comprise an amount of calcium-channel blocking agent from 0.001 mg to 1000 mg, such as 0.01 mg to 500 mg, 0.1 mg to 100 mg, in particular 1 mg to 10 mg, such as 1 mg to 5 mg, e.g. 1 mg, 2 mg, 3 mg, 4 mg, or 5 mg, calculated as the weight of the active compound and exclusive of salt-forming components, or associated water or solvent molecules (for example, calculated as the free base where an acid addition salt is used). When depositing several delivery systems, the systems may have identical or differing contents of calcium-channel blocking agents. Since the delivery system is based on soft, cutable polymers, the size and shape of each single delivery system to be deposited may be trimmed prior to deposition, thus allowing optimal spatial fit and concomitantly the control of the total amount of calcium-channel blocking agent to be deposited. It is within the skill of the physician to determine the total amount to be deposited, depending on factors such as severity of brain trauma, subarachnoidal hemorrhage and/or brain vasospasm, efficacy of the calcium-channel blocking agent, presence of additional active ingredients, or general condition of the subject.

The delivery system of the invention may be used for the manufacture of a medicament for the treatment of brain vasospasm, for example brain vasospasm caused by traumatic brain injury or subarachnoid hemorrhage, as described above.

Methods for Preparing the Delivery System

The delivery systems according to the invention may be produced by a variety of ways known in the art. In a preferred general scheme, manufacture of the delivery system comprises forming a solid dispersion product by preparing a melt of the first poly(lactide-co-glycolide), the second poly(lactide-co-glycolide) and the calcium-channel blocking agent and allowing the melt to solidify, usually after a forming step. In particular, the solid dispersion product may be prepared by melt extrusion. For the production, preferably a blend of a first poly(lactide-co-glycolide), a second poly(lactide-co-glycolide) and one or more calcium-channel blocking agents (and optional ingredients such as further active agents and auxiliary agents) is provided. The aforementioned components are preferably provided having small particle sizes in order to subsequently facilitate the production of a monophase mixture, and may have been milled to appropriate sizes before blending. Alternatively, milling or size reduction can occur after blending. Likewise, some components may be milled separately and added to the other components, optionally followed by further milling or size reduction steps. In case certain components are sticky or elastic at room temperature (such as copolymers of low molecular weight), milling at low temperatures (cryo-milling) can be performed in order to increase their brittleness and facilitate the size reduction process. Calcium-channel blocking agents or active ingredients may be provided in amorphous or crystalline form, preferentially in crystalline, microcrystalline or powder form, and may be ground separately from or together with the other components. Optionally, some components may be provide as melt, while others may be added as solids to the molten mass.

After providing a blend of a milled first poly(lactide-co-glycolide), a milled second poly(lactide-co-glycolide) and a calcium-channel blocking agent (and optional ingredients), the temperature of the blend is increased to a first temperature T1 to obtain a melt. The starting temperature usually may be room temperature or ambient temperature. The temperature increase preferably is rapid and depends on the total mass to be molten (e.g. the feeding compartment of an extruder). For laboratory or small scale extruders, the temperature increase may for example occur within 0.5 to 15 min, such as 0.45 to 5 min, in particular 1 to 3 min, such as within approximately 1 min. For extruders of larger scale with concomitantly higher masses in the feeding compartments that temperature increase may occur over prolonged periods of time, such as 1 to 60 min, 2 to 45 min, 5 to 30 min, or 10 to 20 min. The addition rate of thermal energy should be sufficient to allow efficient melting without the risk of local overheating and concomitant decomposition of copolymers, active ingredients and/or auxiliary agents, and may be determined easily by those skilled in the art. The first temperature T1 depends on the glass transition temperatures of the copolymers, active ingredients and/or auxiliary agents present in the blend and preferably does not exceed the decomposition temperature of any of these components. Preferred ranges for T1 are 80° C.

to 150° C., in particular 80° C. to 160° C., 90° C. to 150° C., 100° C. to 140° C., 110° C. to 130° C., such as for example approximately 120° C., approximately 125° C., approximately 130° C., approximately 135° C., and approximately 145° C. The temperature increase preferably is linear or essentially linear. During the temperature increase to the final temperature T1 the un-molten, partially or completely molten blend can be mixed.

After reaching T1, this temperature is maintained for a period sufficiently long to ensure a complete melting of all components and their complete mixing in order to provide a homogeneous melt with no or essentially no temperature gradient throughout the molten mass. Depending on the total mass of components, the time period may range from 2 min to 30 min, such as 3 min to 25 min, 4 min to 20, or 5 min to 15 min. Preferably the time period is as short as possible in order to avoid thermal damage of the any of the components. A suitable time period may be determined easily by those skilled in the art.

Subsequently the temperature is reduced from T1 to a second temperature T2. The reduction preferably occurs at a linear or essentially linear rate. The temperature reduction should be sufficiently slow to avoid local undercooling and concomitant risk of crystallization or precipitation of one or more components of the melt. Depending on the heat capacity of the melt components and the total mass thereof, the time period for cooling down the melt from T1 to T2 may range from 3 min to 60 min, in particular 4 min to 30 min, 5 min to 20 min, such as 5 min to 10 min. In order to avoid concentration or temperature gradient, the melt is preferably continuously mixed during temperature reduction. T2 is chosen to allow subsequent smooth extrusion by still providing a homogenous melt, sufficient viscosity for passage through an extrusion die at a chosen die pressure, form stability of the extruded mass and suitable solidification times thereof. Depending on the components of the melt, suitable temperatures T2 can easily be determined by those skilled in the art, and may range from 20° C. to 80° C., such as 25° C. to 70° C., in particular 30° C. to 50° C., such as approximately 30° C., approximately 35° C., approximately 40° C. and approximately 45° C.

After reaching T2, the temperature is kept constant for period of time sufficiently long to ensure the equalization of a uniform or essentially uniform temperature T2 throughout the melt. Depending on the total mass of the melt and the components contained therein, the period of time may range from 2 min to 45 min, in particular 3 min to 30 min, 4 min to 20 min, such as approximately 5 min, approximately 10 min or approximately 15 min. In order to accelerate temperature equalization and prevent an non-homogenous distribution of the components of the melt, the melt is preferably mixed during this period.

After reaching a homogenous or essentially homogenous temperature T2 throughout the melt, extrusion occurs by forcing the melt through an extrusion die. Extrusion parameters such as diameter and shape of the die, and extrusion pressure will depend on the desired shape and characteristics of the extrudate, as well as on the characteristics of the melt (depending on the components contained therein), and may be optimized by those skilled in the art. Preferably, the extrudate is a monophasic mixture of the first copolymer, the second copolymer and the at least one active ingredient, and optionally of auxiliary agents, which may be present. In particular, the extrudate is transparent, bubble-free or essentially bubble-free and essentially or completely free of smears upon visual inspection.

Delivery systems of virtually any desired shape may be formed by forcing the melt through a die of suitable shape, optionally followed by an additional molding or forming step, including injection molding, blow molding, extrusion, or any other molding, forming or casting process known in the art to be suitable for shaping components.

During the preparation of the delivery system measures common in the art may be taken to avoid a contamination with contaminating organisms or infectious agents (such as eukaryotic cells, bacteria or viruses) or harmful substances (such as chemicals or endotoxins), followed by packaging in sealed containers or the like ensuring avoidance of subsequent contamination.

The invention will now be further illustrated by the following examples, which are not to be construed as a limitation of the present invention.

EXAMPLES

Example 1

Preparation of Solid Dispersion Products

Blends for preparing solid dispersion products were prepared as follows. The following materials were used:

Resomer® Condensate RG 50:50, $M_n$ 2300 g/mol, obtained from Boehringer Ingelheim Pharma GmbH & Co. KG, Ingelheim, Germany (also referred to as Resomer Mn 2300 herein) which is a copolymer of D,L-lactate and glycolate in a molar ratio from 45:55 to 55:45 and a molecular weight Mn of 2000-2500 g/mol;

Resomer® Condensate RG 50:50, $M_n$ 800 g/mol, obtained from Boehringer Ingelheim Pharma GmbH & Co. KG (also referred to as Resomer Mn 800 herein) which is a copolymer of D,L-lactate and glycolate in a molar ratio from 45:55 to 55:45 and a molecular weight Mn of 800 g/mol;

Nicardipine (free base) was prepared by mixing nicardipine-HCl (Sigma-Aldrich, St. Louis, USA) with water and ethylacetate, then adding 2M NaOH, separating the ethylacetate phase and evaporating the ethylacetate, yielding amorphous nicardipine base as a yellow oily-tough substance. Crystalline nicardipine base was prepared by mixing amorphous nicardipine base and isopropanole/diisopropyl ether, adding seed crystals and cooling on an ice bath over night to allow crystallization. The formed crystals were separated by filtration, washed and dried.

In order to facilitate the handling of Resomer Mn 800, which at room temperature is a waxing, honey-like material, the two copolymers were cryo-milled using a Spex 6700—freezer Mill (5 min, maximum impact frequency) and subsequently mixed by hand using a mortar and a pestle in a cold room (5° C.), additionally including nicardipine.

Three different solid dispersion products were prepared, the composition of which is indicated in Table 1. Additionally, a comparative composition was produced which contained no Resomer Mn 800.

TABLE 1

|  | nicardipine [wt %] | Resomer Mn 2300 [wt %] | Resomer Mn 800 [wt %] |
| --- | --- | --- | --- |
| Composition 1 | 10 | 80 | 10 |
| Composition 2 | 10 | 60 | 30 |
| Composition 3 | 10 | 40 | 50 |
| Comparative Composition | 10 | 90 | 0 |

The blends were converted into solid dispersion products using a RAM-extruder. The RAM-extruder setup was as described in Gurtler et al., J. Controlled Release 33:231-236 (1994). In order to melt the polymers and dissolve the crystalline nicardipine, the blends were rapidly heated to a first temperature T1 of 120° C., and kept at that temperature while mixing was performed. Subsequently, the mixture was cooled down to a second temperature T2 between 35° C. and 45° C., depending on the copolymers, and stably kept at T2 for 10 min. At T2, nicardipine remained soluble in the melt. In order to obtain extrudates with maximum transparency, straightness, homogeneity in diameter and minimum content of air bubbles, the diameter of the extrusion die was selected depending on the respective blend composition as shown in Table 2:

TABLE 2

|  | Composition | | | Comparative Composition. |
| --- | --- | --- | --- | --- |
|  | 1 | 2 | 3 | |
| nicardipine [wt %] | 10 | 10 | 10 | 10 |
| Resomer Mn 2300 [wt %] | 80 | 60 | 40 | 90 |
| Resomer MN 800 [wt %] | 10 | 30 | 50 | 0 |
| die diameter [mm] | 1.75 | 1.75 | 2.00 | 1.75 |
| extrusion pressure [bar] | 4 | 2 | 1 | 2 |
| extrusion temperature T2 [° C.] | 45 | 40 | 35 | 45 |

Figure 1A:
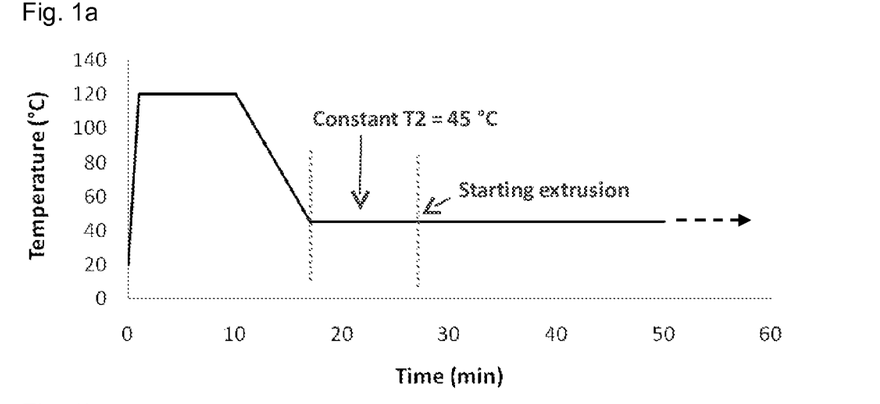
FIG. 1 shows the time and temperature profile of three different melt-extruded solid dispersion products.
Figure 1B:
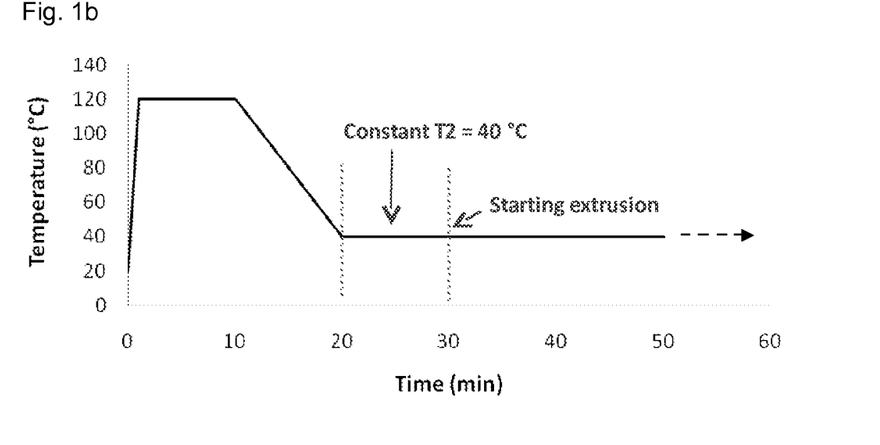
Figure 1C:
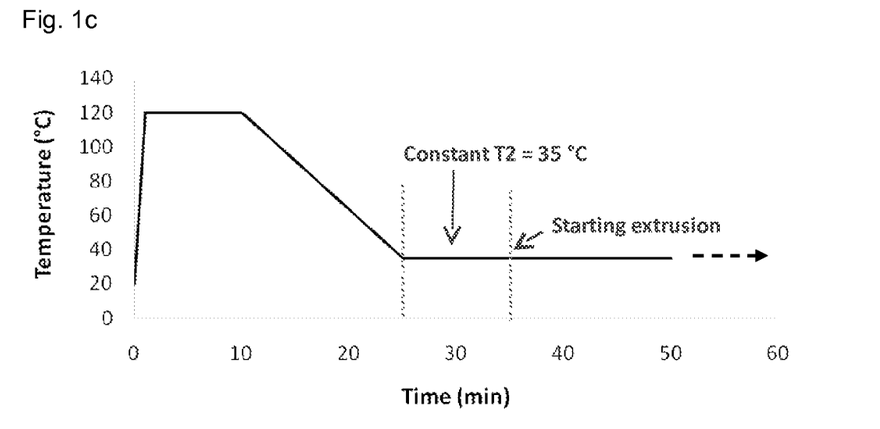

The time and temperature profiles of the extrusions of composition 1, composition 2 and composition 3 are shown in FIG. 1a, FIG. 1b and FIG. 1c, respectively.

The extrudates had a diameter of 2 mm. In order to obtain implants of uniform length (10 mm) and weight (40 mg), the extrudates were cut using a razor blade (at room temperature, without prior heating). The rod-like pieces served as implantable delivery systems according to the invention and were used in further experiments (see below).

Example 2

Determination of Glass Transition Temperatures

The glass transition temperatures of the raw polymers and the solid dispersion products produced in Example 1 above were determined by Differential Scanning calorimetry (DSC) using a SSC/5200 (Seiko, Japan) calorimeter. The analyses were performed by heating from −20° C. to 130° C. (5° C./min) and subsequently cooling down from 130° C. to −20° C. (10° C.). The cycle was repeated one time, values obtained from the repeated cycle are shown in Table 3:

TABLE 3

| Sample | $T_G$ (° C.) |
| --- | --- |
| Resomer Condensate RG50:50 mN 2300 | 25.4 |
| Resomer Condensate RG50:50 mN 800 | 2.0 |
| Comparative composition | 34.2 |
| Composition 1 | 30.6 |
| Composition 2 | 21.1 |
| Composition 3 | 15.5 |

Figure 2:
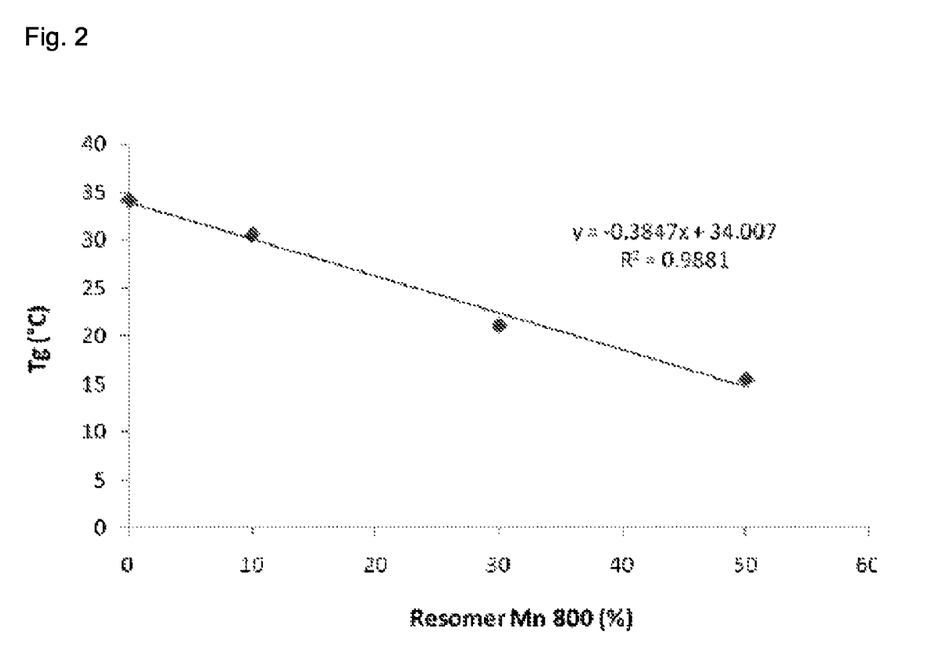
FIG. 2 shows a trend curve demonstrating the relationship of TG and the percentage of Resomer Mn 800 in a solid dispersion product according to the invention (containing 10% nicardipine).

It is obvious that the glass transition temperature $T_G$ decreases as the content of lower molecular weight copolymer Resomer Mn 800 increases. An interpolated trend curve based on the values of Table 2 is shown in FIG. 2 and demonstrates the relationship of $T_G$ and the percentage of Resomer Mn 800.

Example 3

Determination of Nicardipine Content

In order to experimentally verify the nicardipine content of the implants produced in Example 1 above, the implants were dissolved in 50 ml tetrahydrofuran (THF) to obtain as clear solution. 5 vol. % sample were diluted in 95 vol. % mobile phase of an HPLC setup (column: C18 Nucleosil 100-3, 125×4 (inner diameter) mm, plus precolumn C18 Nucleosil 100-3, 8×4 (inner diameter) mm; mobile phase: 10 mM sodium phosphate buffer (pH 5.1): $CH_3CN$=50:50; flow rate: 1 mL/min; temperature: 30° C.; UV-detection at: 240 nm; injection volume: 10 μL). A pump controller "Waters 600E" equipped with a detector "Waters 996 PDA" was used. A calibration curve was obtained from standard solutions containing different nicardipine concentrations in 5% THF and 95% mobile phase. The results are summarized in Table 4 (mean±standard deviation, n=3, CV: coefficient of variation):

TABLE 4

| Sample | Nicardipine content [wt-%] | CV [%] |
| --- | --- | --- |
| Composition 1 | 10.2 ± 0.1 | 0.8 |
| Composition 2 | 10.2 ± 0.2 | 2.3 |
| Composition 3 | 9.7 ± 0.3 | 2.9 |

The experimentally determined nicardipine contents of samples from Composition 1, Composition 2 and Composition 3 are in good agreement with the nominal value of 10 wt. %.

Example 4

Release of Nicardipine from Implants

The release of active ingredient from implants produced in Example 3 was determined by immersing 1 implant in beakers containing 250 mL dissolution medium (phosphate buffered saline, pH 7.4, 0.1 w/v % Tween® 80. The beakers were shaken at 37° C. with a frequency of 60 strokes/min. Samples were taken at predetermined intervals and analysed for nicardipine content by HPLC (column: Luna C18, 150×4.6 [inner diameter] mm+precolumn Luna C18 4×3.0 [inner diameter] mm; mobile phase: 10 mM sodium phosphate buffer (pH 5.1): $CH_3CN$=40:60; flow rate: 1 mL/min; temperature: 30° C.; UV-detection at: 240 nm; injection volume: 10 μL). pump controller "Waters 600E" equipped with a detector "Waters 996 PDA" as described in Example 3 was used, the calibration curve was obtained from standard solutions with different concentrations of nicardipine in 100% mobile phase.

Clinically used reference implants ("Kazuya implants") were used as a control. It is believed that the Kazuya implants were manufactured as described in Kazuya et al., 2002, ibid.).

Figure 3:
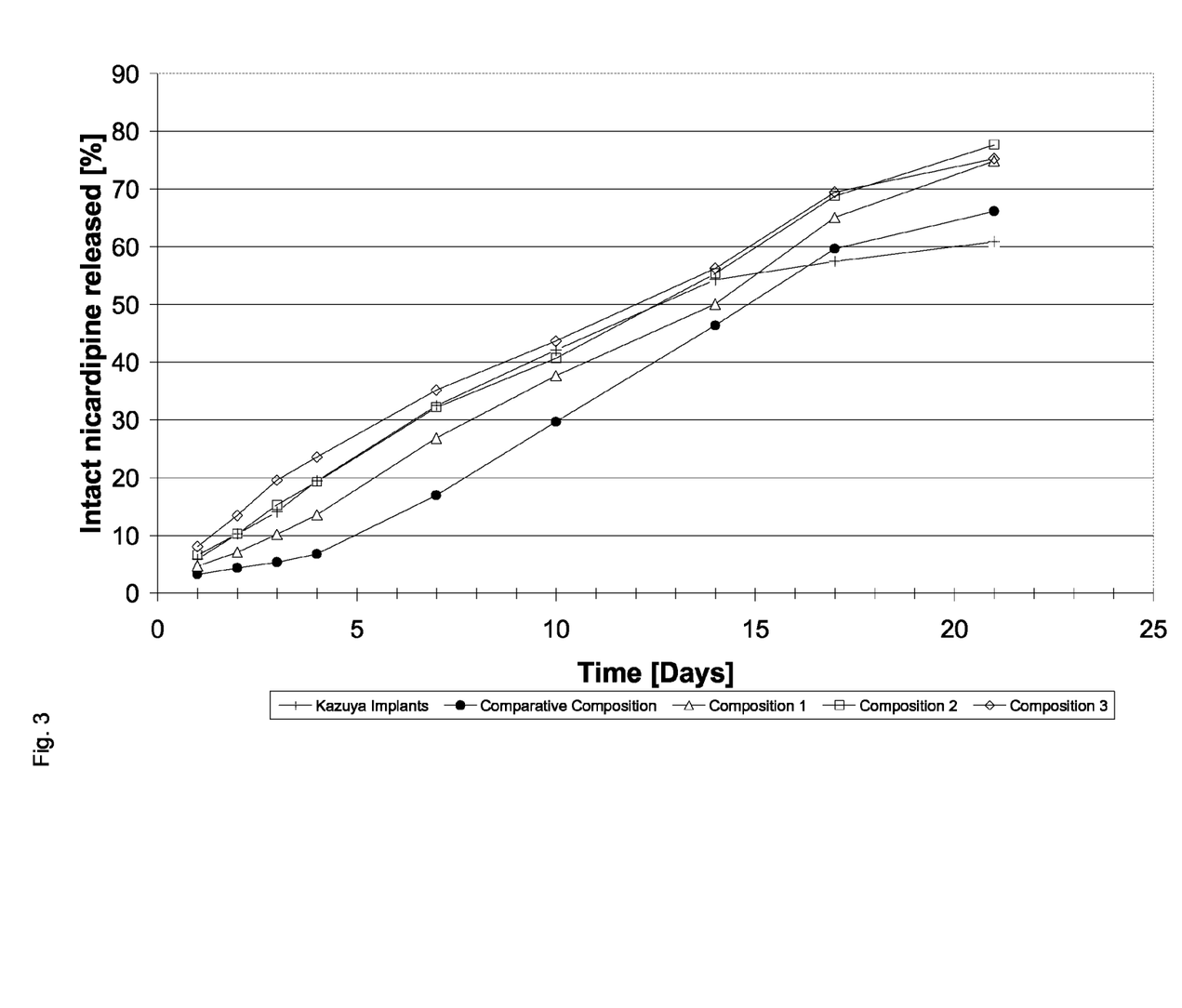
FIG. 3 shows the in vitro-release of nicardipine from implants of different compositions.

The results are shown in FIG. 3. The implant made from the comparative composition displayed a sigmoidal release profile. A 4 days lag time is followed by a relatively rapid nicardipine release. Such a sigmoidal release pattern is generally unwanted in the prevention of brain vasospasm because the available nicardipine concentration during the initial lag time is insufficient. The implants made from the inventive compositions 1 through 3 displayed a more uniform release pattern. The release pattern of compositions 1 and 2 was similar to that of the Kazuya implant; composition 3 even outreached the Kazuya implant. Composition 3, due to its low glass transition temperature, however showed some tackiness which might be a disadvantage in clinical practice.

From FIG. 3 it becomes clear that solid dispersion products containing a first copolymer and a second copolymer can be fine-tuned to effect a slower, identical or higher release of an active ingredient (tested with nicardipine) by varying the relative proportion of the first and the second copolymer. Increasing the proportion of the second copolymer (having a lower molecular weight than the first copolymer) decreases the glass transition temperature and allows for comparatively low glass transition temperatures. Concomitantly, the rate of release proportionally increases with higher contents of the second copolymer in the total composition, while regardless of the ratio of the two copolymers the nicardipine content is uniform. Delivery systems according to the invention thus allow the provision of tailor-made release rates for active ingredients.

We claim:

1. A delivery system for sustained release of nicardipine free base, a hydrate or solvate thereof, adapted for introduction into the cerebrospinal fluid of a subject, comprising a solid dispersion product of nicardipine free base, hydrate or solvate thereof, in a mixture of:
   (i) a first poly(lactide-co-glycolide) having a molecular weight distribution centered around a first number average molecular weight Mn1 and a lactate:glycolate molar ratio of from 45:55 to 55:45; and
   (ii) a second poly(lactide-co-glycolide) having a molecular weight distribution centered around a second number average molecular weight Mn2 and a lactate:glycolate molar ratio in the second poly(lactide-co-glycolide) of from 45:55 to 55:45;
   wherein: Mn1 is in the range of from 2000 to 3000 g/mol and the ratio of Mn1/Mn2 is from 1.8 to 3.5;
   the nicardipine free base, hydrate or solvate thereof is molecularly dispersed in a monophasic mixture comprising the first poly(lactide-co-glycolide) and the second poly(lactide-co-glycolide); and
   the solid dispersion product is formed into a predetermined shape prior to introduction into the cerebrospinal fluid of said subject.

2. The delivery system according to claim 1, wherein the weight ratio of the first poly(lactide-co-glycolide) and the second poly(lactide-co-glycolide) is from 10:1 to 1:1.5.

3. The delivery system according to claim 1, wherein the nicardipine free base, hydrate or solvate thereof constitutes 1 wt. % to 25 wt. % of the total weight of the solid dispersion product.

4. The delivery system according to claim 1, showing an in vitro release profile characterized in that 4.5% to 8.5% of the total amount of nicardipine has been released within 0 and 1 days, 10% to 20% of the total amount of nicardipine has been released within 1 and 3 days, and 25% to 36% of the total amount of nicardipine has been released within 3 and 7 days, when a delivery system containing the equivalent of 4 mg nicardipine is placed in a dissolution medium of phosphate buffered saline, pH 7.4, and 0.1 w/v % polysorbate 80, at 37° C. with shaking at 60 strokes per minute.

5. A method of treatment of brain vasospasm in a subject by depositing a delivery system according to any one of claims 1, 2, 3 and 4 in the cerebrospinal fluid of the subject.

6. The method of treatment according to claim 5, wherein the delivery system is deposited in the vicinity of or adjacent to a blood vessel showing vasospasm or suspected of developing vasospasm.

7. A method for the preparation of a delivery system according to any one of claims 1, 2, 3 and 4, comprising preparing a melt of the first poly(lactide-co-glycolide), the second poly(lactide-co-glycolide) and the nicardipine free base, a hydrate or solvate thereof and allowing the melt to solidify.

8. The method according to claim 7, comprising the steps of:
   a) providing a mixture of the first poly(lactide-co-glycolide), the second poly(lactide-co-glycolide) and the nicardipine free base, a hydrate or solvate thereof,
   b) increasing the temperature of the mixture to a first temperature T1 ranging from 80° C. to 160° C. and maintaining the mixture at the temperature T1 for a period of time ranging from 2 minutes to 30 minutes in order to melt the first and the second poly(lactide-co-glycolide) and to disperse therein the nicardipine free base, hydrate or solvate thereof,
   c) decreasing the temperature to a second temperature T2 ranging from 20° C. to 80° C. and maintaining the mixture at the temperature T2 for a period of time ranging from 2 minutes to 45 minutes in order to adjust the viscosity of the mixture to a viscosity suitable for extrusion, and
   d) forcing the mixture through an extruder die.

* * * * *